United States Patent [19]
Trudell et al.

[11] Patent Number: 5,834,484
[45] Date of Patent: Nov. 10, 1998

[54] COCAINE ANALOGS

[75] Inventors: Mark L. Trudell, New Orleans; Stacey A. Lomenzo, Metairie, both of La.

[73] Assignee: Board of Supervisors of Louisiana State University and Agricultural and Mechanical College, Baton Rouge, La.

[21] Appl. No.: 36,736

[22] Filed: Mar. 9, 1998

Related U.S. Application Data

[60] Provisional application No. 60/084,196 Mar. 12, 1997.
[51] Int. Cl.⁶ .......................... A61K 31/46; C07D 451/02
[52] U.S. Cl. .......................... 514/304; 546/124; 546/132
[58] Field of Search ................................ 546/124, 132; 514/304

[56] References Cited

U.S. PATENT DOCUMENTS 5,374,636  12/1994  Moldt et al. ............................ 514/304

OTHER PUBLICATIONS

Lomenzo et al., "Synthesis, Structure, Dopamine Transporter Affinity, and Dopamine Uptake Inhibition of 6–Alkyl–3–benzyl–2–[(methoxycarbonyl)methyl]tropane Derivatives," *J. Med. Chem.*, vol. 40, No. 26, pp. 4406–4414, Dec. 19, 1997.

D. Simoni et al., "Methoxylation of Cocaine Reduces Binding Affinity and Produces Compounds of Differential Binding and Dopamine Uptake Inhibitory Activity: Discovery of a Weak Cocaine 'Antagonist,'" *J. Med. Chem.*, vol. 36, pp. 3975–3977 (1993).

A.P. Kozikowski et al., "A PLE–Based Resolution of Cocaine, Pseudococaine, and 6– and 7–Methoxylated Cocaine Analogues," *Bioorganic &Medicinal Chemistry Letters*, vol. 6, pp. 441–444 (1996).

A.P. Kozikowski et al., "Synthesis of the 6– and 7–Hydroxylated Cocaines and Pseudococaines," *Tetrahedron Letters*, vol. 37, pp. 5333–5336 (1996).

Z. Chen et al., "Synthesis of 6– or 7– Hydroxy and 6– or 7– Methoxy Tropanes," *Tetrahedron Lett.*, vol. 38, pp. 1121–1124 (1997).

A. Kozikowski et al., "Dipolar Cycloaddition Route to Diverse Analogues of Cocaine: The 6– and 7– Substituted 3–Phenyltropanes," *J. Org. Chem.*, vol. 62, pp. 503–509 (1997).

Lomenzo et al., "A Facile and Efficient Synthesis of (±)–Tropan–2–one," *Synthetic Communications*, vol. 25, pp. 3681–3690 (1995).

*Primary Examiner*—Mukund J. Shah
*Assistant Examiner*—Ann M. Kessinger
*Attorney, Agent, or Firm*—John H. Runnels

[57] ABSTRACT

Cocaine analogs are disclosed. The analogs, certain 6-alkyl substituted tropane derivatives, bind to the cocaine binding site on dopamine transporter, without interfering with the dopamine receptor. The craving for cocaine is thereby blocked. The analogs may readily be synthesized stereoselectively, and are relatively resistant to metabolic degradation.

22 Claims, 2 Drawing Sheets

COCAINE ANALOGS

The development of this invention was funded by the Government under grant R29 DA08055 awarded by the National Institute on Drug Abuse. The Government has certain rights in this invention.

The benefit of the, Mar. 12, 1997 filing date of provisional application Ser. No. 60/084,190, now abandoned, is claimed under 35 U.S.C. § 119(e).

This invention pertains to compositions and methods for treating cocaine addiction, particularly to cocaine antagonists or low-level agonists that reduce the craving for cocaine.

The abuse of cocaine is a major national and international health problem. There has been considerable effort to try to understand the pharmacology and behavioral effects of cocaine.

So-called dopaminergic neurons in the brain use dopamine to transmit signals between neurons. A presynaptic neuron releases dopamine into a synapse between neurons. From the synaptic gap dopamine binds to receptors on a postsynaptic neuron, completing the circuit. Dopamine transporter ("DAT") then moves dopamine from the synapse back to the presynaptic neuron, which re-uptakes dopamine to be used again.

It is generally accepted that cocaine binds to DAT, thus blocking the re-uptake of dopamine into presynaptic neurons. When dopamine is not resorbed by presynaptic neurons, artificially high levels of dopamine remain in synapses, causing over-firing of postsynaptic neurons. It is the overfiring of postsynaptic neurons that is believed to be responsible for cocaine's stimulant effects and behavioral effects. The abnormally high levels of dopamine in the synapse are then metabolically removed, reducing overall dopamine levels. The reduced dopamine levels are believed to be responsible for craving after the cocaine itself is metabolized, accounting for cocaine's addictive character.

To treat cocaine addiction, it would be desirable to have an effective cocaine antagonist that interferes with cocaine's binding to DAT, without interfering with DAT's ability to transport dopamine. Such an antagonist would have little or no effect on the dopamine neurotransmitter cycle, but it would block the stimulatory effects of cocaine, and would also eliminate physical craving for cocaine. The cocaine binding site on DAT is not identical to the dopamine receptor, although bound cocaine does sterically or allosterically block the dopamine receptor. There is a need for cocaine antagonists that will bind at the cocaine binding site on DAT, without interfering with dopamine re-uptake.

Cocaine, compound 1 in FIG. 1, is a substituted tropane, specifically, 2β-carbomethoxy-β3β-benzoxytropane.

Several tropane and non-tropane analogs have been tried as potential treatments for cocaine addiction. Compound 2 (FIG. 1), a disubstituted piperazine derivative (GBR 12909), and the tropane derivatives 6β-methoxypseudococaine (Compound 3) and 7β-methoxypseudococaine (Compound 4) have been reported to have potential as therapeutic agents for cocaine abuse.

D. Simoni et al., "Methoxylation of Cocaine Reduces Binding Affinity and Produces Compounds of Differential Binding and Dopamine Uptake Inhibitory Activity: Discovery of a Weak Cocaine 'Antagonist,'" *J. Med. Chem.*, vol. 36, pp. 3975–3977 (1993) describes the synthesis of analogs having methoxy substituents at the 6 and 7 positions of cocaine and pseudococaine (e.g., Compounds 3 and 4 of FIG. 1 of the present specification). (Pseudococaine is the 2α-carbomethoxy diastereomer of cocaine.) Some of these compounds were reported to be weak in vitro antagonists for cocaine. However, the binding affinities of compounds 3 and 4 to DAT were relatively low. See also A. P. Kozikowski et al., "A PLE-Based Resolution of Cocaine, Pseudococaine, and 6- and 7-Methoxylated Cocaine Analogues," *Bioorganic & Medicinal Chemistry Letters*, vol. 6, pp. 441–444 (1996); and A. P. Kozikowski et al., "Synthesis of the 6- and 7-Hydroxylated Cocaines and Pseudococaines," *Tetrahedron Letters*, vol. 37, pp. 5333–5336 (1996).

The stereoselective synthesis of certain 6-alkyl tropanes is mentioned in S. A. Lomenzo et al., "Stereoselective Synthesis of 6-Alkyl Tropanes," Abstracts of American Chemical Society, 211th National Meeting, Division of Organic Chemistry, Abstract No. 289 (Mar. 24–28, 1996).

Z. Chen et al., "Synthesis of 6- or 7-Hydroxy and 6- or 7-Methoxy Tropanes," *Tetrahedron Lett.*, vol. 38, pp. 1121–1124 (1997) discloses the synthesis of certain 6- and 7-substituted tropanes.

A. Kozikowski et al., "Dipolar Cycloaddition Route to Diverse Analogues of Cocaine: The 6- and 7-Substituted 3-Phenyltropanes," *J. Org. Chem.*, vol. 62, pp. 503–509 (1997) discloses the synthesis of certain 6- and 7-substituted 3-phenyltropanes.

No effective cocaine antagonists have previously been identified. Previously reported low-activity cocaine agonists have low potency, or are short-lived in vivo, limiting their usefulness.

Novel cocaine analogs have been discovered. The novel analogs, certain 6-alkyl substituted tropane derivatives as specified below, bind to the cocaine binding site on DAT. The novel compounds are potent, long-lived cocaine analogs useful in treating cocaine addiction and overdoses. The analogs may readily be synthesized stereoselectively, and are relatively resistant to metabolic degradation.

A note on nomenclature: In this specification, compounds are sometimes referred to by arabic numerals. The numerals correspond to the structures of FIGS. 1 and 2. Compound 4, for example, is the compound in FIG. 1 designated "4." Some of the compounds in FIG. 2 have additional letter designations. The letters refer to the substituents shown in the box at the bottom of FIG. 2. For example Compound 12b is the compound in FIG. 2 designated "12," in which the "R" group shown is methyl.

A common feature of the novel analogs is that they bear a substituent comprising H—; or an alkyl group of 4 carbon atoms or fewer; or a phenyl, benzyl, methoxycarbonyl, or hydroxymethyl group at the 6α- or 6β-position of the tropane heterocylic bridge structure in cocaine. A second common feature of the novel analogs is that the carbomethoxy substituent at the 2β-position of the tropane structure in cocaine is replaced by a methoxycarbonylmethyl substituent at either the 2β-position or the 2α-position of the tropane structure. A third common feature of the novel analogs is that the benzoxy substituent at the 3β-position of the tropane structure in cocaine is replaced by a substituted or unsubstituted benzyl group.

The novel analogs are represented generically as Compounds 5 and 6, in which "R" denotes H—, an alkyl group of 4 carbons or fewer, phenyl, benzyl, methoxycarbonyl, or hydroxymethyl at the 6α- or 6β-position; and in which "X," "Y," and "Z" each denote H—, F—, Cl—, or $CH_3$—; and in which at least two of the substituents X, Y, and Z are H—. The nomenclature for the novel agonists is 6(α or β)-R-3β-benzyl-2(α or β)-(methoxycarbonylmethyl)-8-methyl-8-azabicyclo[3.2.1]octane; wherein R is a group as just described; and wherein the benzyl group may have an X, Y, or Z substituent as just described.

In vitro data have shown that several of these compounds bind tightly to the cocaine binding site of DAT. In vivo experiments will be performed in the near future.

Figure 1:
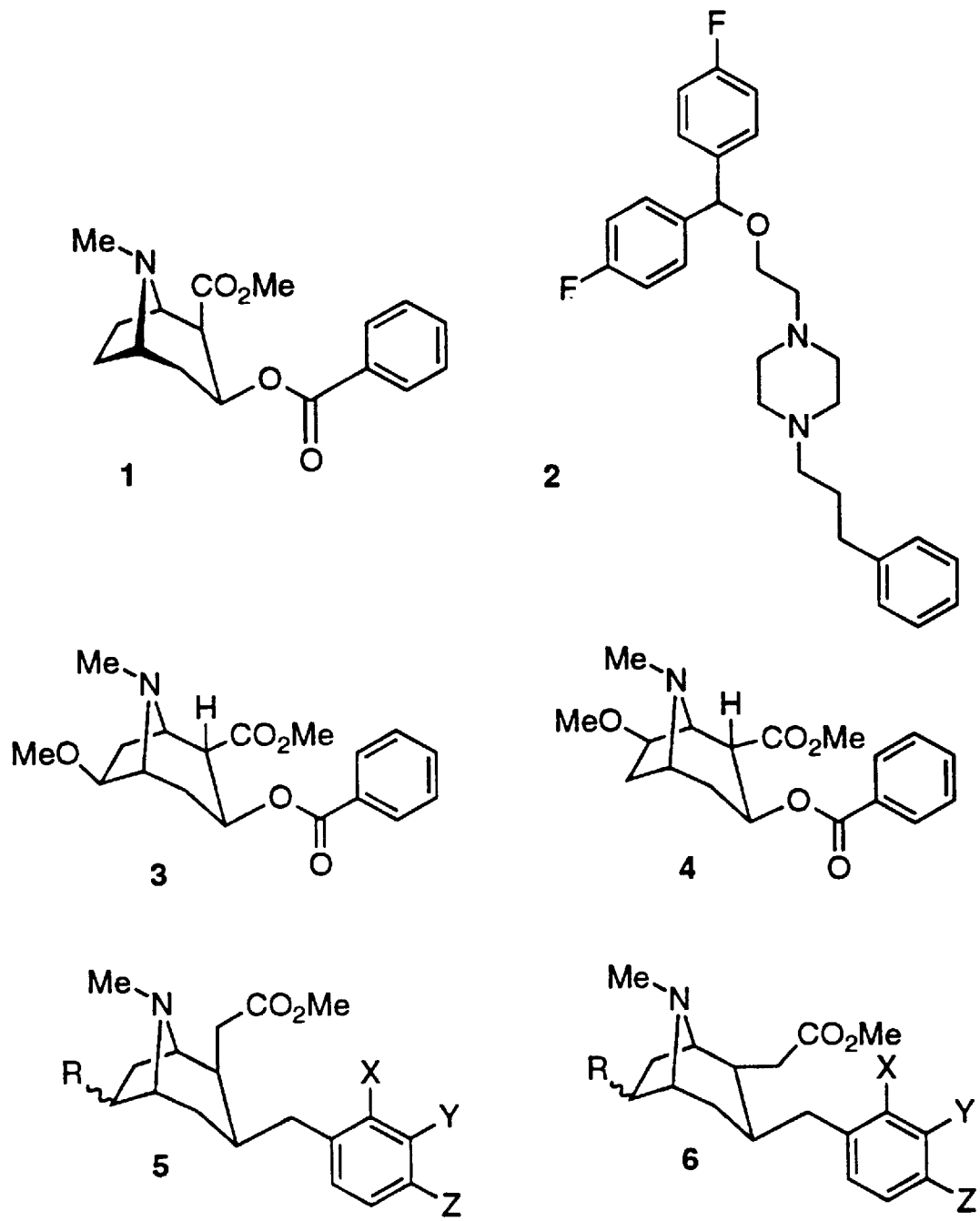
FIG. 1 depicts cocaine, certain prior art analogs of cocaine, and the novel cocaine analogs of the present invention.
Figure 2:
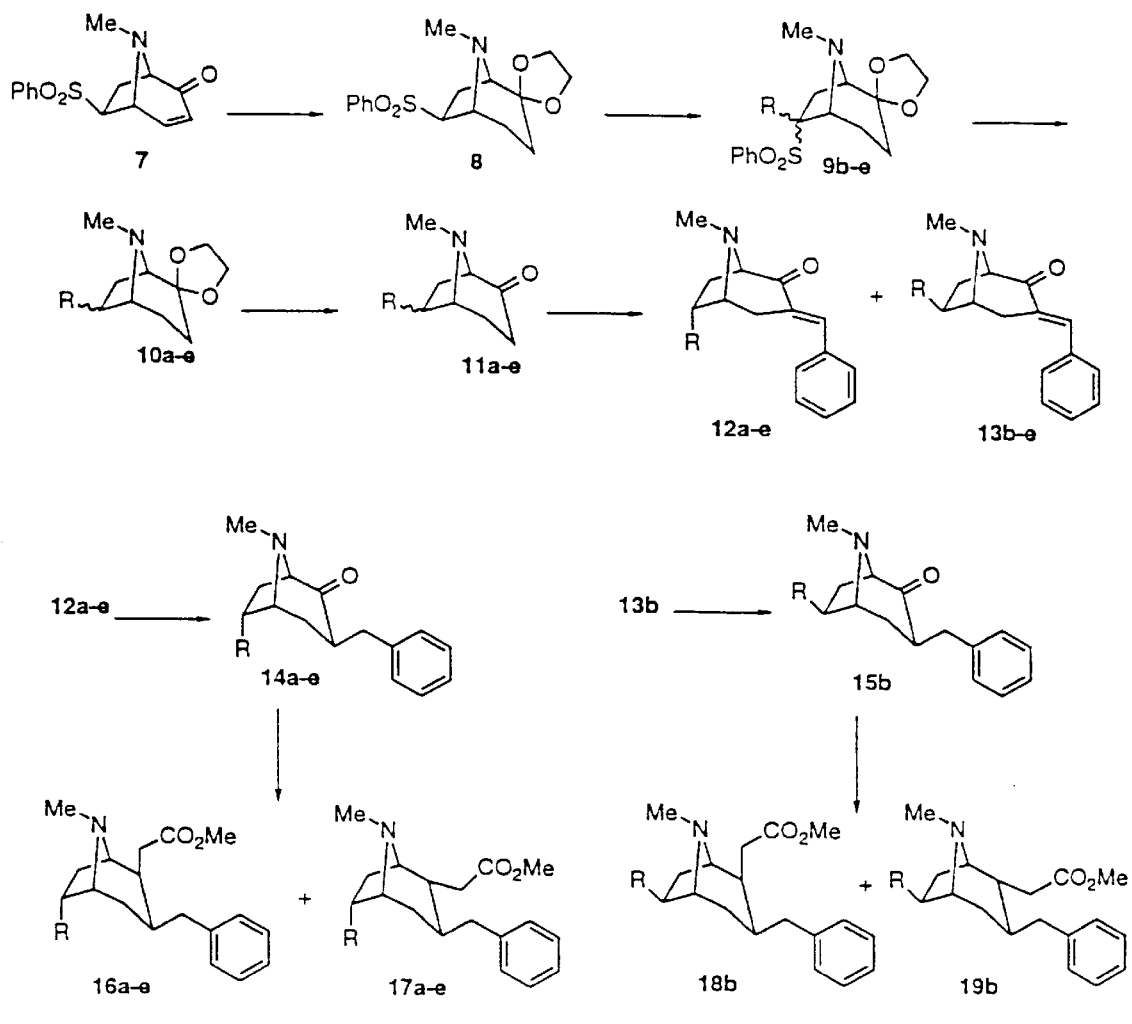
FIG. 2 depicts synthetic routes for the novel cocaine analogs of the present invention.

Several 6-alkyl-3β-benzyl-2-(methoxycarbonylmethyl)-tropane derivatives 5 and 6 were synthesized and used to investigate the effect of substitution at the 6-position on the binding affinity of the novel cocaine- and pseudococaine-derivatives.

The 3β-benzyl group is believed to be essentially bioisosteric with the 2β-benzoyl group of cocaine, but less susceptible to metabolic degradation. Similarly, the 2-methoxycarbonylmethyl group does not substantially affect binding affinity relative to that for the 2-methoxycarbonyl group of both cocaine and pseudococaine. (We found introducing the 2-methoxycarbonyl methyl to be synthetically more efficient than addition of a 2-methoxycarbonyl group, without substantially affecting the compound's affinity relative to cocaine.)

Synthesis

Our synthesis began with Compound 7, which was converted into Compound 8, both as described in S. A. Lomenzo et al., "A Facile and Efficient Synthesis of (±)-Tropan-2-one," *Synthetic Communications*, vol. 25, pp. 3681–3690 (1995). Compound 7 was converted into Compound 8 in a two-step process: (1) reaction with $H_2$ over Pd/graphite in $CH_3CH_2OH/CHCl_3$; and (2) reaction with $HOCH_2CH_2OH$ in p-tosyl alcohol and benzene over heat. The synthesis of various 6-alkyl tropane derivatives then proceeded by alkylation/desulfonylation of Compound 8, 6β-benzenesulfonyl-8-methyl-8-azabicyclo-[3.2.1]octan-2-one ethylene acetal.

Compound 8 was treated with n-butyllithium at −78° C. in dry THF, followed by addition of the appropriate alkyl halide at 0 C., to produce the corresponding alkylated sulfone derivatives 9b–e as a mixture of diastereomers in high yields (Table 1). The 6α-benzenesulfonyl isomers 9b–e were determined by NMR and x-ray crystallography to be the major products, although the relative yields varied with different alkyl substituents.

TABLE 1

Stereoselectivity and Reaction Yields for the Alkylation of Compound 8, for the Desulfonylation of Compounds 8 and 9b–e, and for the Olefination/Hydrogenation of Compounds 14a–e.

| | Alkylation of Compound 8 | | | Desulfonylation of Compounds 8 and 9b–e | | | Olefination and Hydrogenation of Compounds 14a–e[a] | | |
|---|---|---|---|---|---|---|---|---|---|
| | | 6α:6β | | | | | | 16:17 | |
| R | cmpd | ratio[b,c] | yield (%) | cmpd | 6α:6β[d] | yield (%) | cmpd | ratio[e] | yield (%)[f] |
| H | | NA | NA | 10a | NA | 85 | 16a/17a | 1:2 | 68 |
| Me | 9b | 3:2 | 98 | 10b | 3:1 | 85 | 16b/17b | 1:3 | 55 |
| Et | 9c | 3:2 | 96 | 10c | 3:1 | 91 | 16c/17c | 1:3 | 47 |
| n-Pr | 9d | 5:2 | 80 | 10d | 5:1 | 87 | 16d/17d | 1:4 | 65 |
| n-Bu | 9e | 5:2 | 76 | 10e | 6:1 | 83 | 16e/17e | 1:5 | 78 |

Footnotes to Table 1: (a) The E- and Z-isomer ratios of the products of the olefination step were not determined. (b) Orientation refers to the benzenesulfonyl group. (c) Isomer ratios were determined by $^1$H NMR and HPLC. (d) Isomer ratios were determined by $^1$H NMR. (e) Isomer ratios were determined from isolated yields. (f) Overall yield; reactions conditions were not optimized.

The sulfonyl carbanion of Compound 8 appeared to have little influence on the stereochemistry of the reaction. For the tropane system, the steric effects experienced by the approaching electrophile appeared to govern the selectivity of the alkylation. Therefore, because the β-face was more accessible, the product resulting from β-alkylation dominated.

Compound 8 and its alkylated products 9b–e were desulfonylated with 40% Na(Hg) in $Na_2HPO_4$-buffered methanol/THF to produce the corresponding tropane derivatives 10a–e in high yields (80–91%) as a mixture of diastereomers. (See Table 1.) The 6α-isomers of Compounds 10b–e were the major products, resulting from kinetic quench of the intermediate radical species generated by reductive C-S cleavage in situ.

Tropane derivatives 10a–e were converted into the corresponding tropanone derivatives 11a–e (72–87% yield) by reaction with 3N $HClO_4$ at 90° C. The tropanone derivatives 11a–e were then condensed with benzaldehyde in 5N NaOH in ethanol to give the benzylidene derivatives 12a–e and 13a–e (70–82% yield). The 6α- and 6β-isomers of Compounds 12b–e and 13b–e were easily separated by column chromatography on a flash silica gel column (silica gel 60, 230–400 mesh, E.M. Science). Hydrogenation of the carbon-carbon double bond of Compounds 12a–e or 13b–e over Pd/graphite in ethanol stereoselectively yielded the 3β-benzyl derivatives 14a–e. Wadsworth-Emmons olefination of the ketones 14a–e (reaction with NaH and $(CH_3O)_2POCH_2CO_2CH_3$ in 1,2-dimethoxyethane (DME) at 80° C.), followed by hydrogenation of the intermediate alkylidine esters over Pd/graphite in ethanol afforded a mixture of the 2α- and 2β-isomers 16a–e and 17a–e with good overall yields (see Table 1). The isomers were easily separated by chromatography on a flash silica gel column, and were converted into the corresponding salts to make them readily soluble in aqueous buffer solutions. The choices of salts were based simply on which salts readily formed solid crystalline materials. The nature of the salt does not substantially affect the biological activity. Compounds 16a–e and 17a–e were oxalate salts $(C_2H_2O_4)$; Compounds 18b and 19b were fumarate salts $(C_4H_4O)$; and Compounds 18d and 19d were hydrochloride salts (HCl).

The minor benzylidine isomer 13b was converted by substantially similar reaction steps into Compound 15b, and then to the 6β-methyl analogs 18b and 19b (66% overall yield, ratio of 18b:19b=2:7).

In vitro Studies

WIN 35,065-2 and WIN 35,428 are potent cocaine analogs. [$^3$H]WIN 35,428 is a radiolabelled form of WIN 35,428 commonly used as a standard to measure the binding affinity of cocaine ligands. WIN 35,065-2 (not illustrated) is structurally identical to cocaine, except that the 3β-benzoxy group is replaced with a 3β-phenyl group. WIN 35,428 (not illustrated) is structurally identical to WIN 35,065-2, except that the para-hydrogen on the phenyl group is replaced with a fluorine atom. "[$^3$H] WIN 35,428" designates WIN 35,428 in which a tritium atom replaces each of the 3 hydrogen atoms bonded to the carbon atom at the 9-position of the tropane ring, i.e., the methyl group that is bonded to the nitrogen atom is per-tritiated.

Compounds 16a–e, 17a–e, 18b, 18d, 19b, and 19d were each tested for their ability to displace [$^3$H]WIN 35,428 bound to tissue from the caudate-putamen region of the rat brain. The $K_i$ values reported in Table 2 for the unlabeled ligands 16a–e, 17a–e, 18b, 18d, 19b, and 19d are dissociation constants derived for the unlabelled ligands. The $K_i$ values reported in Table 2 for cocaine and WIN 35,065-2 were taken from S. Izenwasser et al., "Differential Relationships among Dopamine Transporter Affinities and Stimulant Potencies of Various Uptake Inhibitors," *Eur. J. Pharm.*, vol. 263, pp. 277–283 (1994), whose experiments were performed under substantially identical conditions. As noted by Izenwasser et al., cocaine and WIN 35,065-2 modeled better as having two binding sites rather than just one; therefore, both their high affinity and low affinity $K_i$ values are given in Table 2.

TABLE 2

Inhibition of [$^3$H]WIN 35,428 Binding.

| compound | R | Formula[a] | $K_i$ (nM)[b] |
|---|---|---|---|
| cocaine | | | 32 ± 5 |
| | | | 338 ± 221 |
| WIN 35,065-2 | | | 33 ± 17 |
| | | | 314 ± 222 |
| 16a | H | $C_{18}H_{25}NO_2 \cdot C_2H_2O_4$ | 91 ± 10 |
| 16b | Me | $CH_{19}H_{22}NO_2 \cdot C_2H_2O_4$ | 211 ± 11 |
| 16c | Et | $C_{20}H_{29}NO_2 \cdot C_2H_2O_4$ | 307 ± 9 |
| 16d | n-Pr | $C_{21}H_{31}NO_2 \cdot C_2H_2O_4$ | 4,184 ± 10 |

TABLE 2-continued

Inhibition of [$^3$H]WIN 35,428 Binding.

| compound | R | Formula[a] | $K_i$ (nM)[b] |
|---|---|---|---|
| 16e | n-Bu | $C_{22}H_{dd}NO_2 \cdot C_2H_2O_4$ | 8,579 ± 5 |
| 17a | H | $C_{18}H_{25}NO_2 \cdot C_2H_2O_4$ | 108 ± 14 |
| 17b | Me | $C_{19}H_{27}NO_2 \cdot C_2H_2O_4$ | 531 ± 12 |
| 17c | Et | $C_{20}H_{29}NO_2 \cdot C_2H_2O_4$ | 1,147 ± 12 |
| 17d | n-Pr | $C_{21}H_{31}NO_2 \cdot C_2H_2O_4$ | 7,241 ± 19 |
| 17e | n-Bu | $C_{22}H_{33}NO_2 \cdot C_2H_2O_4$ | 19,658 ± 12 |
| 18b | Me | $C_{19}H_{27}NO_2 \cdot C_2H_2O_4$ | 57 ± 9 |
| 18d | n-Pr | $C_{23}H_{31}NO_2 \cdot HCl$ | 5,852 ± 702 |
| 19b | Me | $C_{19}H_{27}NO_2 \cdot C_2H_2O_4$ | 294 ± 10 |
| 19d | n-Pr | $C_{23}H_{31}NO_2 \cdot HCl$ | 57,340 ± 3,440 |

Footnotes to Table 2: (a) Microanalyses were within ± 0.4 of theoretical values. The "ligands" designate the corresponding acid used to form the salt. (b) All values are mean ± standard error of the mean for three experiments performed in triplicate.

The binding affinity of the racemic unsubstituted analog 16a was not statistically different from the binding affinities of cocaine and WIN 35,065-2; all had high affinity $K_i$ values. The unsubstituted 2α-isomer 17a was significantly less potent. The binding affinities of the 6α-alkyl-2β-(methoxycarbonylmethyl) congeners 16b–e decreased as the size of the alkyl substituent increased. The 6α-alkyl-2α-(methoxycarbonyl-methyl) congeners 17b–e showed a similar trend, although their binding affinities were lower than those of the corresponding 2β-congeners 16b–e.

It is noteworthy that the racemate 6β-methyl-2β-(methoxycarbonylmethyl) isomer 18b had a binding affinity within a factor of two of the high affinity binding components of cocaine and WIN 35,065-2. In addition, Compound 18b had only a slightly lower binding affinity than that of the unsubstituted analog 16a, and was about fourfold more potent than the corresponding 6α-methyl analog 16b. The 6β-methyl-2α-(methoxy-carbonylmethyl) congener 19b had a binding affinity comparable to that of the unsubstituted derivative 17a, and was about twice as potent as the corresponding 6α-isomer 17b. From these observations we conclude that substitution in the 6β-position does not inhibit binding as strongly as does substitution in the 6α-position.

The novel 6-alkyl-3β-benzyl-2α-(methoxycarbonylmethyl)-tropane derivatives 17b–c and 19b had considerably stronger binding affinities than those of the prior art cocaine analogs 3 and 4. The binding affinities of Compounds 17a and 19b,d were nearly three orders of magnitude more potent than that of Compound 3, while the isosteric ethyl analog 17c was about 100 times more potent than Compound 3.

Studies underway include investigating the ability of Compounds 16a, 16b, 17a, 17b, 18a, and 19a to inhibit dopamine reuptake. Additional studies will include resolution of analogs into the enantiopure (1R, 5S)- and (1S, 5R)-stereoisomers, and the evaluation of those stereoisomers in both in vitro studies and in vivo assessment of behavioral effects.

In vivo Experiments

The higher in vitro binding affinities of the 6-alkyl-3β-benzyl-2α-(methoxycarbonylmethyl)-tropane congeners suggests that in vivo studies now underway will show them to be more potent cocaine antagonists than Compounds 3 and 4. The ability of the congeners 16a–c, 18b, the 2α-isomers 17a–c, and 19b to inhibit dopamine reuptake is currently under investigation. The most promising candidates as identified by the initial in vivo studies will be resolved into the enantiopure (1R, 5S)-stereoisomers or (5R, 5S)-stereoisomers for further in vitro and in vivo studies.

Each of the novel cocaine analogs will be assayed for several types of biological activity known to be correlated with the abuse potential of cocaine and cocaine-like compounds. All compounds will be assessed for binding to dopamine transporter (DAT) labeled with [$^3$H] WIN 35,428. This binding site is closely associated with the site responsible for the reinforcing effects of cocaine. See M. C. Ritz et al., "Cocaine Receptors on Dopamine Transporters are Related to Self-Administration of Cocaine," *Science*, vol. 237, pp. 1219–1223 (1987). Prior studies have indicated that drugs with high affinity for DAT have reinforcing effects, and that they are more potent in producing reinforcing effects than are compounds with lower affinity for DAT.

In addition, the compounds will be tested in a standard assay for psychomotor stimulation in rodents. Compounds with stimulant effects produce large dose-related increases in locomotor activity. An initial confirmation may then be made of the relation between binding characteristics of the compounds and their behavioral activity.

Subsequent tests will examine substitution of the compounds in rats that have been trained to discriminate injections of cocaine from injections of saline. This test is a model of the subjective effects of cocaine. Previous studies have indicated that a compound's ability to induce discriminative effects similar to those of cocaine is directly related to the compound's affinity for the dopamine transporter binding site. E. J. Cline et al., "Stimulus Generalization from Cocaine to Analogs with High In Vitro Affinity for Dopamine Uptake Sites," *Behavioural Pharmacology*, vol. 3, pp. 113–116 (1992). This assay will also be used to assess the pharmacological equivalence of the analogs and cocaine in a more specific behavioral procedure. Again, agreement between in vitro assessments of affinity at the dopamine transporter and discriminative stimulus effects will be assessed.

Compounds with high DAT affinity but low behavioral effects are examined further. First, the possibility needs to be examined that a compound might not be active in behavioral tests due to poor bioavailability. Bioavailability will be assayed by examining in vivo displacement of [$^3$H] WIN 35,428. Compounds with adequate bioavailability, relatively high affinity for DAT, and little or no behavioral activity show high promise as antagonists of both the locomotor activity and discriminative effects of cocaine, and will be tested further in monkeys.

Compounds will also be examined for their reinforcing effects in primates. In these studies, newly synthesized compounds will be substituted in subjects trained to self-administer cocaine according to standard procedures. Outcomes of these studies are most directly related to the abuse liability of the tested drugs. These are labor-intensive, time-consuming studies and therefore initial studies will examine only selected compounds. Subsequent studies will be initiated depending on initial results, and on structure-activity considerations. Certainly, any compound with potential antagonist activity will be examined under these procedures in order to assess its potential to antagonize the reinforcing effects of cocaine. If the results of the trials in monkeys are encouraging, clinical trials in humans will be conducted.

Pharmacological Assays—Detailed Methods

Displacement of [$^3$H] WIN 35,428 Binding.

Rat striatal membranes are prepared from frozen tissue with slight modifications from the method of J. A. Javitch et al., "[$^3$H]Mazindol Binding Associated with Neuronal Dopamine and Norepinephrine Uptake Sites," *Mol. Pharmacol.*, vol. 26, pp. 35–44 (1984). Brains are immediately removed from sacrificed rats, and the striatum, cerebral cortex, and hippocampus are dissected free. Tissues are homogenized in buffer to estimate the density of dopamine uptake sites. Brain tissue is homogenized in 50 volumes of ice cold tissue buffer (50 mM Tris HCl containing 120 mM NaCl, 5 mM KCl, pH 7.4, 0° C.) for 20 seconds using a Brinkman Polytron™ at setting 5. The homogenate is centrifuged, resuspended, and centrifuged again. After the second centrifugation the tissue pellet is resuspended in the same buffer (pH 7.4 at 22° C.) at a concentration of 15 mg original wet weight per ml. To estimate the density of dopamine uptake sites in the various brain regions, tissue homogenate (100 μL) is added to glass test tubes containing [$^3$H] WIN 35,428 at a saturating concentration of 1.0 nM, and incubated at 22° C. for one hour in a final volume of 1.0 ml buffer. Mazindol (2.0 μM) is used to determine non-specific binding. The assay is terminated by rapidly filtering the suspension over Whatman GF/C filters previously soaked in 0.05% polyethyleneimine to reduce non-specific binding, and washing the filters with 3×5.0 ml assay buffer.

Behavioral Studies.

Adult male Sprague-Dawley rats (Charles River, Wilmington, Mass.) or adult squirrel monkeys (*Saimiti sciureus*) are subjects in studies of locomotor activity and cocaine discrimination. All subjects have unrestricted access to water in a temperature-controlled animal housing room under a 12 hr light/dark cycle. For studies of cocaine discrimination, subjects are food-deprived and maintained at 350 g by post-session feeding in separate living cages. Monkeys are used in studies of drug self-administration. All behavioral testing is conducted during the light phase. All governing protocols and guidelines for animal experimentation are followed.

Locomotor Activity.

Rats are observed in Digiscan™ activity monitors (Omnitech Electronics, Columbus, Ohio), (40 cm)$^3$ clear acrylic chambers equipped with photoelectric detectors placed 2.56 cm apart along the walls of the chamber. One activity count is registered each time a subject crosses two different beams. Repetitive interruptions of the same beam (e.g. grooming, head bobbing, etc.) are not counted. Rats are individually habituated to the chamber for 30 minutes, removed briefly, injected, and placed back in the apparatus for a 30-minute observation period. Each dose is studied in eight rats. The ED-50 dose (i.e., the dose at which a response is elicited in 50% of tested subjects) for each compound is obtained by recording the time course effects of each over a 4-hour period (N=6 per group).

Cocaine Discrimination.

Training and testing sessions are conducted in two-lever operant-conditioning test chambers (BRS/LVE, model RTC-022) housed within light- and sound-attenuating enclosures. White noise is present throughout testing, and ambient illumination is provided by a lamp in the top center of the front wall of the chamber (houselight). Levers are set 17 cm apart, with red lamps above the left lever and white lamps above the right lever. A downward force of 0.2N on either lever produces an audible "click" and is recorded as a response. Reinforced responses cause one 45 mg food pellet (BioServ) to be delivered to a centrally located food tray.

Rats are trained, as described in E. J. Cline et al., "Stimulus Generalization from Cocaine to Analogs with High In Vitro Affinity for Dopamine Uptake Sites," *Behavioural Pharmacology*, vol. 3, pp. 113–116 (1992) to respond by pressing one lever after the injection of 10 mg/kg cocaine, and pressing the other lever after injection of saline. The cocaine and saline levers are counterbalanced (left lever versus right lever) across subjects. Sessions start with a 5-minute period during which no stimulus lights are illuminated in the chamber, and during which any responses are disregarded. After the 5-minute timeout, the houselight and the lights over the levers are turned on. Twenty consecutive responses on the appropriate lever are rewarded by a food pellet, followed by a 20-second timeout period; even a single response on the inappropriate lever resets counting for the 20-response requirement. A maximum of 20 food pellets are delivered during a 15 minute test session. Satisfactory training is defined as a correct overall response rate of at least 85%.

Cocaine- and saline-training sessions are conducted in an "ABBA" sequence, with test sessions interposed between repetitions of a particular type. A test session is conducted if the subject meets the performance criteria on both of the immediately preceding saline- and cocaine-training sessions. During test sessions, a range of doses of cocaine or the novel compounds are substituted for cocaine or saline. Test sessions are identical to training sessions, with the exception that 20 consecutive responses on either lever produces a food pellet.

Self-administration.

During experimental sessions, subjects are seated in a Plexiglass restraint chair similar to those described previously in J. E. Barrett, "Behavioral Pharmacology of the Squirrel Monkey" in L. A. Rosenblum et al. (eds), *Handbook of Squirrel Monkey Research*, pp. 315–348 (1985). The chair is enclosed within a sound-attenuating chamber during sessions. Mounted in front of the subject is a response key (model 121-05, BRS/LVE Corp., Beltsville, N. Mex.) on which a downward force of at least 0.27N produces an audible click upon a relay, and is recorded as a response. Pairs of red, green, and amber lamps (6 W, 115 V a.c.) are mounted at eye level and are individually illuminated to serve as visual stimuli.

A motor-driven syringe is located outside the experimental chamber, and is connected to an implanted catheter by Teflon® tubing that passes through a small port in the chamber wall. The syringe is driven by a 115-V a.c. motor, which is held motionless between injections by a small d.c. voltage. Each activation of the motor produces a 0.18 ml, 200 msec injection through the catheter.

Subjects are initially trained to press the response key with cocaine reinforcement in the presence of red stimulus lights. Each press on the lever produces an injection of cocaine (10 to 30 µg/kg per injection, depending on the subject). During cocaine injections the red stimulus lights are turned off, and the green stimulus lights are illuminated for the 200 msec duration of the injection. After reliable lever pressing has been achieved, a brief (10 second) timeout period is introduced following each injection; during this timeout period all stimulus lights are off, and any lever pressing is disregarded. Over the course of several daily sessions, the number of responses for a subject to be rewarded with an injection is increased, and the timeout period is lengthened. Following several sessions of training with injections following 3 responses, the value is rapidly increased to a final value of 30 responses, and the timeout duration is increased to one minute.

When reliable responses are achieved and maintained at the 30-response level, sessions are introduced in which saline is injected. During the saline-injection sessions, all other conditions are identical to those of the sessions in which cocaine is injected. Saline sessions alternate with cocaine sessions in a double-alternation sequence. With some subjects it is necessary to present saline on several consecutive sessions to obtain reliable decreases in response rates as compared to the cocaine sessions. All subjects are eventually studied under the double-alternation sequence, with high response rates maintained for cocaine and low response rates for saline.

Once performances stabilize under the double-alteration sequence, effects of the test compounds are assessed. Sessions in which test compounds are examined are scheduled between repeat sessions of cocaine or saline during the double alternation sequence. Test sessions are not conducted if performances are not appropriate (i.e., low response rates during a cocaine session or high response rates during a saline session) during the preceding two control sessions (one cocaine and one saline). Each dose of each test drug is examined at least once in each of at least three different subjects.

Human Clinical Trials.

Following the successful conclusion of trials in animals, in vitro and in vivo clinical trials for treating cocaine addictions and cocaine overdoses in human patients will be conducted in accordance with applicable laws and regulations. See, e.g., H. Schoemaker et al., "Sodium dependent [$^3$H]cocaine binding associated with dopamine uptake sites in rat striatum human putamen decrease after dopaminergic denervation and in Parkinson's disease," *Naunyn. Schmiedebergs Arch. Pharmacol.*, vol. 329, pp. 227–235 (1985); and N. Volkow et al., "Relationship between psychostimulant-induced 'high' and dopamine transporter occupancy," *Proc. Natl. Acad. Sci.* USA, vol. 93, pp. 10388–10392 (1996).

Miscellaneous

As used in the Claims, an amount of a cocaine analog is considered to be "therapeutically effective" if it blocks the stimulatory effects of cocaine, to a clinically significant degree; or if it reduces the addictive craving induced by cocaine, to a clinically significant degree. As used in the Claims, the term "cocaine analog" includes compounds that are antagonists of the effects of cocaine in the central nervous system, or that are low-level agonists of cocaine.

The complete disclosures of all references cited in this specification are hereby incorporated by reference. In the event of an otherwise irreconcilable conflict, however, the present specification shall control.

We claim:

1. 6-R-3β-(X-benzyl)-2-R'-8-methyl-8-azabicyclo[3.2.1]octane;

wherein the 6-R substituent is 6α-methyl, 6β-methyl, 6α-ethyl, 6β-ethyl, 6α-n-propyl, 6β-n-propyl, 6α-isopropyl, 6β-isopropyl, 6α-n-butyl, 6β-n-butyl, 6α-s-butyl, 6β-s-butyl, 6α-t-butyl, 6β-t-butyl, 6α-phenyl, 6β-phenyl, 6α-benzyl, 6β-benzyl, 6α-methoxycarbonyl, 6β-methoxycarbonyl, 6α-hydroxymethyl, or 6β-hydroxymethyl;

wherein the 2-R' substituent is 2α-(methoxycarbonylmethyl) or 2β-(methoxycarbonylmethyl); and wherein the X substituent is in the ortho-, meta-, or para-position of the 3β-(X-benzyl) group, and wherein the X substituent is H—, F—, Cl—, or CH₃—.

2. A compound as recited in claim 1, wherein said compound is 6α-methyl-3β-benzyl-2α-(methoxycarbonylmethyl)-8-methyl-8-azabicyclo[3.2.1]octane.

3. A compound as recited in claim 1, wherein said compound is 6α-methyl-3β-benzyl-2β-(methoxycarbonylmethyl)-8-methyl-8-azabicyclo[3.2.1]octane.

4. A compound as recited in claim 1, wherein said compound is 6β-methyl-3β-benzyl-2α-(methoxycarbonylmethyl)-8-methyl-8-azabicyclo[3.2.1]octane.

5. A compound as recited in claim 1, wherein said compound is 6β-methyl-3β-benzyl-2β-(methoxycarbonylmethyl)-8-methyl-8-azabicyclo[3.2.1]octane.

6. A compound as recited in claim 1, wherein said compound is 6α-ethyl-3β-benzyl-2α-(methoxycarbonylmethyl)-8-methyl-8-azabicyclo[3.2.1]octane.

7. A compound as recited in claim 1, wherein said compound is 6α-ethyl-3β-benzyl-2β-(methoxycarbonylmethyl)-8-methyl-8-azabicyclo[3.2.1]octane.

8. A compound as recited in claim 1, wherein said compound is 6β-ethyl-3β-benzyl-2α-(methoxycarbonylmethyl)-8-methyl-8-azabicyclo[3.2.1]octane.

9. A compound as recited in claim 1, wherein said compound is 6β-ethyl-3β-benzyl-2β-(methoxycarbonylmethyl)-8-methyl-8-azabicyclo[3.2.1]octane.

10. A compound as recited in claim 1, wherein said compound is the enantiomer (1R, 5S)-6-R-3β-(X-benzyl)-2-R'-8-methyl-8-azabicyclo[3.2.1]octane.

11. A compound as recited in claim 1, wherein said compound is the enantiomer (1S, 5R)-6-R-3β-(X-benzyl)-2-R'-8-methyl-8-azabicyclo[3.2.1]octane.

12. A method of treating a human patient suffering from cocaine addiction or from a cocaine overdose, comprising administering to the patient a therapeutically effective amount of a cocaine analog, wherein the cocaine analog is 6-R-3β-(X-benzyl)-2-R'-8-methyl-8-azabicyclo[3.2.1]octane;

wherein the 6-R substituent is 6α-methyl, 6β-methyl, 6α-ethyl, 6β-ethyl, 6α-n-propyl, 6β-n-propyl, 6α-isopropyl, 6β-isopropyl, 6α-n-butyl, 6β-n-butyl, 6α-s-butyl, 6β-s-butyl, 6α-t-butyl, 6β-t-butyl, 6α-phenyl, 6β-phenyl, 6α-benzyl, 6β-benzyl, 6α-methoxycarbonyl, 6β-methoxycarbonyl, 6α-hydroxymethyl, or 6β-hydroxymethyl;

wherein the 2-R' substituent is 2α-(methoxycarbonylmethyl) or 2β-(methoxycarbonylmethyl); and wherein the X substituent is in the ortho-, meta-, or para-position of the 3β-(X-benzyl) group, and wherein the X substituent is H—, F—, Cl—, or CH₃—.

13. A method as recited in claim 12, wherein the compound is 6α-methyl-3β-benzyl-2α-(methoxycarbonylmethyl)-8-methyl-8-azabicyclo[3.2.1]octane.

14. A method as recited in claim 12, wherein the compound is 6α-methyl-3β-benzyl-2β-(methoxycarbonylmethyl)-8-methyl -8-azabicyclo[3.2.1]octane.

15. A method as recited in claim 12, wherein the compound is 6β-methyl-3β-benzyl-2α-(methoxycarbonylmethyl)-8-methyl-8-azabicyclo[3.2.1]octane.

16. A method as recited in claim 12, wherein the compound is 6β-methyl-3β-benzyl-2β-(methoxycarbonylmethyl)-8-methyl-8-azabicyclo[3.2.1]octane.

17. A method as recited in claim 12, wherein the compound is 6α-ethyl-3β-benzyl-2α-(methoxycarbonylmethyl)-8-methyl-8-azabicyclo[3.2.1]octane.

18. A method as recited in claim 12, wherein the compound is 6α-ethyl-3β-benzyl-2β-(methoxycarbonylmethyl)-8-methyl-8-azabicyclo[3.2.1]octane.

19. A method as recited in claim 12, wherein the compound is 6β-ethyl-3β-benzyl-2α-(methoxycarbonyl methyl) -8-methyl -8-azabicyclo [3.2.1]octane.

20. A method as recited in claim 12, wherein the compound is 6β-ethyl-3β-benzyl-2β-(methoxycarbonylmethyl)-8-methyl-8-azabicyclo[3.2.1]octane.

21. A method as recited in claim 12, wherein the compound is the enantiomer (1R, 5S)-6-R-3β-(X-benzyl)-2-R'-8-methyl-8-azabicyclo[3.2.1]octane.

22. A method as recited in claim 12, wherein the compound is the enantiomer (1S, 5R)-6-R-3β-(X-benzyl)-2-R'-8-methyl-8-azabicyclo[3.2.1]octane.

* * * * *